US011400237B2

(12) United States Patent
Lee

(10) Patent No.: US 11,400,237 B2
(45) Date of Patent: Aug. 2, 2022

(54) MEDICINE INFUSION APPARATUS INCLUDING THERMOELECTRIC MODULE

(71) Applicant: IMPACT KOREA CO., LTD., Anyang-si (KR)

(72) Inventor: Moung Sook Lee, Anyang-si (KR)

(73) Assignee: IMPACT KOREA CO., LTD., Anyang-si (KR)

( * ) Notice: Subject to any disclaimer, the term of this patent is extended or adjusted under 35 U.S.C. 154(b) by 281 days.

(21) Appl. No.: 16/612,811

(22) PCT Filed: Jul. 2, 2019

(86) PCT No.: PCT/KR2019/008041
§ 371 (c)(1),
(2) Date: Nov. 12, 2019

(87) PCT Pub. No.: WO2021/002497
PCT Pub. Date: Jan. 7, 2021

(65) Prior Publication Data
US 2021/0353880 A1 Nov. 18, 2021

(51) Int. Cl.
*A61M 5/44* (2006.01)
*A61M 5/148* (2006.01)
(Continued)

(52) U.S. Cl.
CPC .............. *A61M 5/44* (2013.01); *A61M 5/148* (2013.01); *A61M 5/16813* (2013.01);
(Continued)

(58) Field of Classification Search
CPC .. A61M 5/152; A61M 5/142; A61M 5/14224; A61M 5/148
See application file for complete search history.

(56) References Cited

U.S. PATENT DOCUMENTS 5,399,166 A * 3/1995 Laing .................. A61M 5/1483
604/131
6,175,688 B1 * 1/2001 Cassidy ................ A61M 5/365
392/470
(Continued)

FOREIGN PATENT DOCUMENTS

KR 10-2006-0019623 A 3/2006
KR 10-2019-0057988 A 5/2019

*Primary Examiner* — Manuel A Mendez
(74) *Attorney, Agent, or Firm* — KORUS Patent, LLC; Seong Il Jeong

(57) ABSTRACT

Provided is a medicine infusion apparatus capable of infusing a liquid medicine into a human body by using a medicine container configured to discharge the liquid medicine contained therein, along a designated path when a pressure is applied from outside, the medicine infusion apparatus including one or more medicine pressing units including one or more inflatable parts capable of being inflated by air to apply a pressure to the medicine container, a first pumping unit capable of inflating one of the inflatable parts by including a first pump capable of generating air of a preset pressure, and a first pipe connectable to the one of the inflatable parts, and a heating unit including a thermoelectric module capable of heating the medicine within a preset temperature range. According to the present invention, the medicine infusion apparatus may be produced as a compact portable apparatus by using a low-capacity battery and be used for emergencies at accident sites where electricity may not be easily supplied.

9 Claims, 11 Drawing Sheets

(51) Int. Cl.
*A61M 5/168* (2006.01)
*A61M 5/145* (2006.01)

(52) U.S. Cl.
CPC ............ *A61M 2005/14506* (2013.01); *A61M 2205/362* (2013.01); *A61M 2205/3673* (2013.01); *A61M 2205/8206* (2013.01)

(56) References Cited

U.S. PATENT DOCUMENTS

2018/0112666 A1\* 4/2018 Dreifert .................. F04C 25/02
2018/0142808 A1\* 5/2018 Oh ............................ F17D 1/14

\* cited by examiner

MEDICINE INFUSION APPARATUS INCLUDING THERMOELECTRIC MODULE

TECHNICAL FIELD

The present invention relates to a medicine infusion apparatus, and more particularly, to a medicine infusion apparatus that may be produced as a compact portable apparatus by using a low-capacity battery and be used for emergencies at accident sites where electricity may not be easily supplied.

BACKGROUND ART

A fluid is a sort of medical liquid to be infused into a human body to treat a shock, dehydration, malnutrition, or the like, and includes blood and various electrolyte solutions isotonic with blood, e.g., a physiological saline and a Ringer's solution.

The fluid is a medical liquid to be infused through a vein of a patient for an operation or therapy or to treat a shock, dehydration, or malnutrition, and may include, for example, blood, an electrolyte solution, and a medicine similar to blood and, more specifically, a physiological saline, a Ringer's solution, a parenteral nutrition solution, and an intravenous fluid which are isotonic with human body fluids.

In general, a fluid bag such as a medicine container B illustrated in FIG. 3 is hanged upside down above a human body and a medicine is infused into the human body through a tube T and a needle N connected to the medicine container B.

A surgical patient or an emergency patient requires infusion of various medicines. A high-risk medicine needs to be precisely infused by a small dose at a designated timing, and medicine infusion apparatuses such as piston-type and syringe-type medicine infusion apparatuses have been developed for this purpose.

However, unlike the high-risk medicine, a low-risk medicine such as the fluid needs to be infused by a large dose at a high pressure. A general medicine infusion apparatus configured to precisely infuse a high-risk medicine by a small dose may control a medicine infusion rate but may not easily infuse a medicine at a high pressure, and thus may not infuse a low-risk medicine such as a fluid at a high pressure by a large dose. Furthermore, the general medicine infusion apparatus has a complex structure or usage, and thus may have a high failure rate and a very high total manufacturing cost.

In addition, the general medicine infusion apparatus needs to complexly and inconveniently calculate a flow rate and a flow velocity whenever constant maintenance of a high pressure or urgent pressure adjustment is required, and thus may cause great inconvenience to a user or a patient.

Besides, the general medicine infusion apparatus may cause inconvenience of heating the fluid to a temperature similar to a body temperature by using a heater such as a heating cabinet or a warmer before infusion of the fluid, and may also cause inconvenience of carrying a heavy and large high-capacity battery for a place where electricity is not supplied, because high energy is required to instantaneously heat the fluid by using hot wire or hot water.

DETAILED DESCRIPTION OF THE INVENTION

Technical Problem

The present invention provides a medicine infusion apparatus that may be produced as a compact portable apparatus by using a low-capacity battery and be used for emergencies at accident sites where electricity may not be easily supplied.

Technical Solution

According to an aspect of the present invention, there is provided a medicine infusion apparatus capable of infusing a liquid medicine into a human body by using a medicine container configured to discharge the liquid medicine contained therein, along a designated path when a pressure is applied from outside, the medicine infusion apparatus including one or more medicine pressing units including one or more inflatable parts capable of being inflated by air to apply a pressure to the medicine container, a first pumping unit capable of inflating one of the inflatable parts by including a first pump capable of generating air of a preset pressure, and a first pipe connectable to the one of the inflatable parts, and a heating unit including a thermoelectric module capable of heating the medicine within a preset temperature range.

The medicine infusion apparatus may further include a second pumping unit capable of inflating one of the inflatable parts by including a second pump capable of generating air of a preset pressure, and a second pipe connectable to the one of the inflatable parts.

The medicine infusion apparatus may further include a connection unit including a connection pipe for interconnecting the first and second pipes, and a connection pipe valve capable of opening or closing the connection pipe, and one or more inflatable parts connected to the first and second pipes may be inflated by operating one of the first and second pumps when another of the first and second pumps does not operate.

The medicine infusion apparatus may further include a first upstream valve provided at an upstream side of the first pipe, a first downstream valve provided at a downstream side of the first pipe, a second upstream valve provided at an upstream side of the second pipe, and a second downstream valve provided at a downstream side of the second pipe, and the connection pipe may have one end connected to the first pipe between the first upstream valve and the first downstream valve, and another end connected to the second pipe between the second upstream valve and the second downstream valve.

The heating unit may include a heating space capable of accommodating a tube, in which the medicine flows, to be isolated from outside, and the thermoelectric module may heat air contained in the heating space and the heated air may indirectly heat the tube.

The tube may be densely arranged at a preset density or above in the heating space.

The heating unit may include a tube fixer capable of detachably fixing a tube in which the medicine flows.

The tube fixer may include a gripping part including a hollow hole capable of accommodating the tube, and being elastically deformable, and an insertion part provided at one end of the hollow hole to serve as a passage through which the tube is inserted into the hollow hole.

The heating unit may include a heating unit body including a heating space capable of accommodating a tube, in which the medicine flows, to be isolated from outside, and a heating unit cover capable of changing positions between a closed position for closing the heating space and an open position for opening the heating space, and through holes capable of detachably accommodating the tube may be provided in at least one of the heating unit body and the heating unit cover.

The heating unit cover of the heating unit may be coupled to the heating unit body by hinges to be rotatable between the closed position and the open position.

The medicine infusion apparatus may receive electricity supplied by a replaceable or rechargeable battery.

Advantageous Effects of the Invention

According to the present invention, an medicine infusion apparatus capable of infusing a liquid medicine into a human body by using a medicine container configured to discharge the liquid medicine contained therein, along a designated path when a pressure is applied from outside includes one or more medicine pressing units including one or more inflatable parts capable of being inflated by air to apply a pressure to the medicine container, a first pumping unit capable of inflating one of the inflatable parts by including a first pump capable of generating air of a preset pressure, and a first pipe connectable to the one of the inflatable parts, and a heating unit including a thermoelectric module capable of heating the medicine within a preset temperature range, and thus may be produced as a compact portable apparatus by using a low-capacity battery and be used for emergencies at accident sites where electricity may not be easily supplied.

BEST MODE

Hereinafter, the present invention will be described in detail by explaining embodiments of the invention with reference to the attached drawings.

Figure 1:
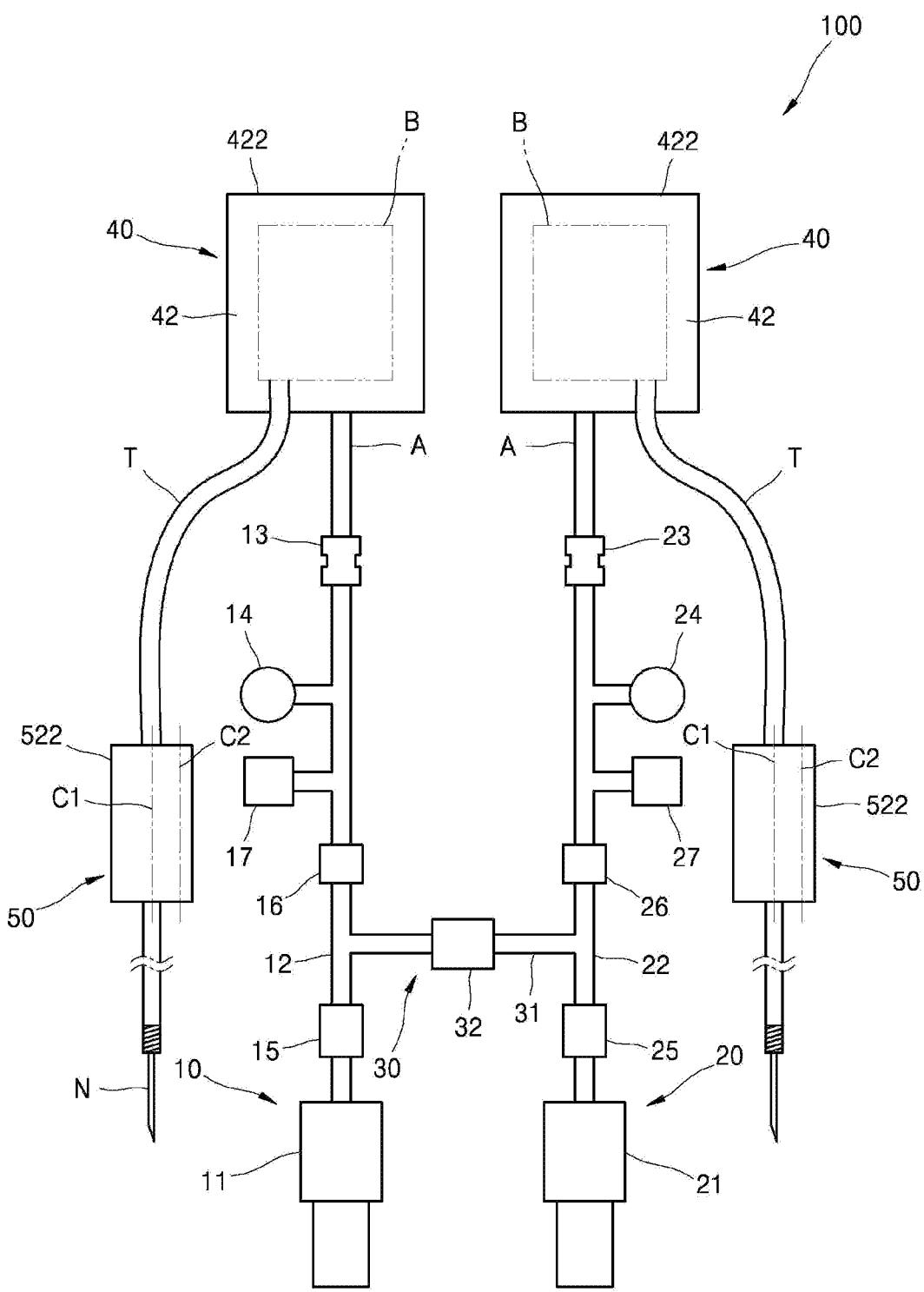
FIG. 1 is a front view of a medicine infusion apparatus according to a first embodiment of the present invention.
Figure 2:
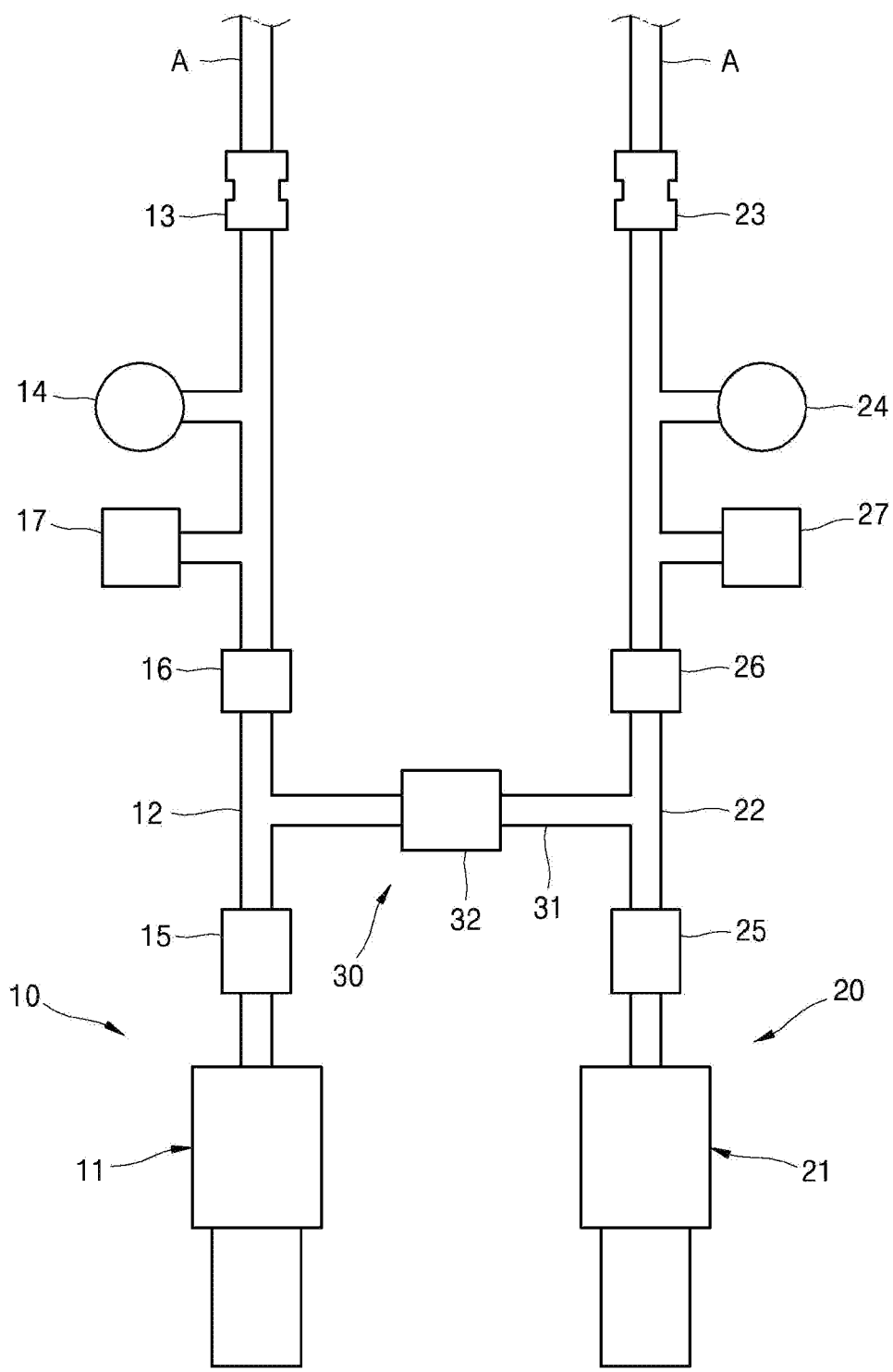
FIG. 2 is a front view of a first pumping unit and a second pumping unit illustrated in FIG. 1.
Figure 3:
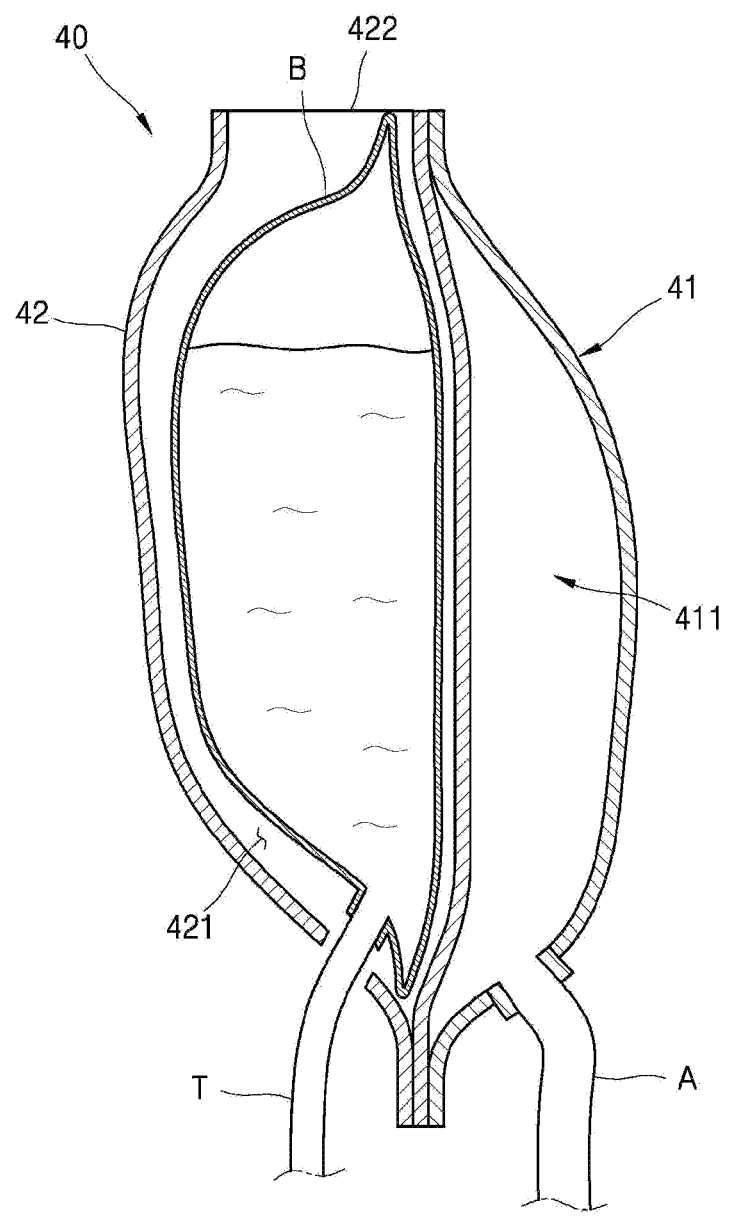
FIG. 3 is a vertical cross-sectional view of a medicine pressing unit illustrated in FIG. 1.

FIG. 1 is a front view of a medicine infusion apparatus 100 according to a first embodiment of the present invention, and FIG. 2 is a front view of a first pumping unit 10 and a second pumping unit 20 illustrated in FIG. 1. FIG. 3 is a vertical cross-sectional view of a medicine pressing unit 40 illustrated in FIG. 1.

Referring to FIGS. 1 to 3, the medicine infusion apparatus 100 according to an embodiment of the present invention is a medicine infusion apparatus capable of infusing a liquid medicine such as a fluid into a human body, uses medicine containers B each configured to discharge the liquid medicine contained therein, along a designated path when a pressure is applied from outside, and includes the first pumping unit 10, the second pumping unit 20, a connection unit 30, the medicine pressing units 40, and heating units 50. The following description assumes that the medicine containers B have a flexible synthetic resin bag shape. In this case, the medicine container B are generally produced in a transparent or translucent bag shape by using synthetic resin such as polyvinyl chloride, polybutadiene, or polystyrene.

The first pumping unit 10 is an apparatus capable of inflating an inflatable part 41 of the medicine pressing unit 40, and includes a first pump 11, a first pipe 12, and a first outlet 13.

The first pump 11 is an air pump operating by electricity, and may generate air of a preset pressure.

The first pipe 12 is a pipe having one end connected to the first pump 11 and the other end connectable to the inflatable part 41.

In the current embodiment, the first pipe 12 includes a circular synthetic resin tube.

The first outlet 13 is provided at the other end of the first pipe 12, and is a hole for discharging the air supplied from the first pump 11.

The first outlet 13 is connected to an air tube A connected to the inflatable part 41.

At an upstream side of the first outlet 13, a first sensor 14 capable of measuring an internal air pressure of the first pipe 12 is mounted as illustrated in FIG. 1.

At an upstream side of the first sensor 14, a first exhaust valve 17 for discharging air stored in an internal space 411 of the inflatable part 41, to outside in an emergency, e.g., a case when an internal air pressure of the inflatable part 41 is excessively high or a case when the first pump 11 operates over a set time, is mounted.

In the current embodiment, the first exhaust valve 17 includes a 1-way solenoid valve operating by electricity, and is normally closed.

At an upstream side of the first exhaust valve 17, a first downstream valve 16 capable of opening or closing the first pipe 12 to or not to allow the air to flow in the first pipe 12 is mounted.

In the current embodiment, the first downstream valve 16 includes a 2-way solenoid valve operating by electricity.

When the first downstream valve 16 is closed, the pressed air may not flow into the inflatable part 41 and the air in the inflatable part 41 may not flow backward into the first pump 11.

At an upstream side of the first downstream valve 16, a first upstream valve 15 capable of opening or closing the first pipe 12 to or not to allow the air to flow in the first pipe 12 is mounted.

In the current embodiment, the first upstream valve 15 includes a 2-way solenoid valve operating by electricity.

When the first upstream valve 15 is closed, the pressed air generated from the first pump 11 may not flow toward the first downstream valve 16 and the air in the first pipe 12 connected to a connection pipe 31 may not flow backward into the first pump 11.

Like the first pumping unit 10, the second pumping unit 20 is an apparatus capable of inflating the inflatable part 41 of the medicine pressing unit 40, and includes a second pump 21, a second pipe 22, a second outlet 23, a second sensor 24, a second upstream valve 25, a second downstream valve 26, and a second exhaust valve 27.

In the current embodiment, the second pump 21, the second pipe 22, the second outlet 23, the second sensor 24, the second upstream valve 25, the second downstream valve 26, and the second exhaust valve 27 of the second pumping unit 20 are the same as or correspond to the first pump 11, the first pipe 12, the first outlet 13, the first sensor 14, the first upstream valve 15, the first downstream valve 16, and the first exhaust valve 17 of the first pumping unit 10, respectively, and thus detailed descriptions thereof are not provided herein.

The connection unit 30 is an apparatus for interconnecting the first and second pipes 12 and 22, and includes the connection pipe 31 and a connection pipe valve 32.

The connection pipe 31 is a pipe for interconnecting the first and second pipes 12 and 22, and has one end connected to the first pipe 12 between the first upstream valve 15 and the first downstream valve 16 of the first pipe 12, and the other end connected to the second pipe 22 between the second upstream valve 25 and the second downstream valve 26 of the second pipe 22.

The connection pipe valve 32 is a valve capable of opening or closing the connection pipe 31 to or not to allow the air to flow in the connection pipe 31.

In the current embodiment, the connection pipe valve 32 includes a 2-way solenoid valve operating by electricity.

The medicine pressing unit 40 is an apparatus capable of pressing the medicine container B, and a pair of the medicine pressing units 40 are separately connected to the first and second pumping units 10 and 20. Each of the medicine pressing units 40 includes the inflatable part 41 and a medicine container holder 42.

The inflatable part 41 is an inflatable part having a sealable internal space 411, and is configured to inflate as illustrated in FIG. 3 when the air is injected into the internal space 411.

The internal space 411 of the inflatable part 41 is connected to each of the first and second outlets 13 and 23 by the air tube A as illustrated in FIGS. 1 and 3.

In the current embodiment, the inflatable part 41 has a rectangular bag shape produced by combining two sheets of synthetic resin film, but may also have an arbitrary bag shape such as a circular or polygonal bag shape.

In the current embodiment, a pressure of the inflatable part 41 may be adjusted to a value desired by a user, e.g., 100 mmHg, 200 mmHg, or 300 mmHg.

The inflatable part 41 is configured to apply a pressure to the medicine container B when the air is injected into the internal space 411.

The inflatable part 41 may be made of a material that does not easily burst when inflated.

The medicine container holder 42 is a part having an internal space 421 capable of accommodating the medicine container B.

The medicine container holder 42 is in contact with a bottom surface of the inflatable part 41 as illustrated in FIG. 3.

At one end of the medicine container holder 42, a medicine container slot 422 for inserting or taking the medicine container B into or out of the internal space 421 is provided.

The medicine container holder 42 may have a material and a thickness not to be easily stretchable when the inflatable part 41 inflates to press the medicine container B. When the medicine container holder 42 is made of an easily stretchable material, although the inflatable part 41 inflates, the medicine container B may not be sufficiently pressed.

Figure 4:
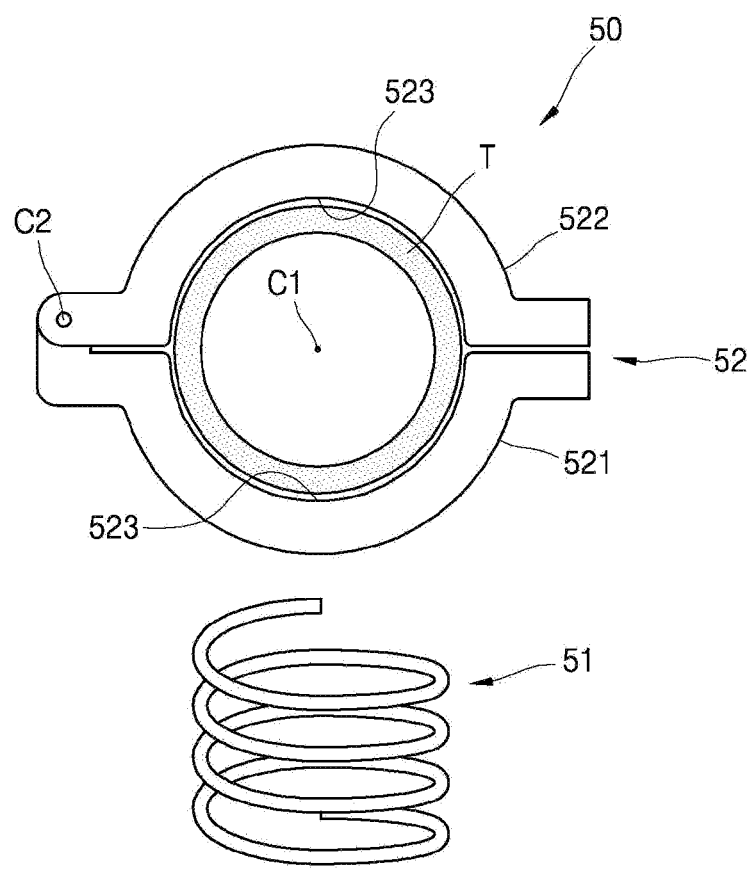
FIG. 4 is a top view of a heating unit illustrated in FIG. 1.

Each of the heating units 50 is an apparatus for heating the medicine discharged from the medicine container B, within a preset temperature range, operates based on induction heating (IH), and includes a magnetic field generator 51 and a heater 52 as illustrated in FIG. 4.

The magnetic field generator 51 is a part for generating a magnetic field near the heater 52, and may include a coil through which electricity flows.

The heater 52 is a part including a metal heated by a current induced by the magnetic field generated by the magnetic field generator 51, and includes a heater body 521, a heater cover 522, and tube accommodating grooves 523.

The heater body 521 is a member extending along a first central axis C1 as illustrated in FIGS. 1 and 4, and includes a semicircular tube accommodating groove 523 configured to surround and accommodate a lower part of a circular tube T.

The tube T is a circular tube in which the medicine flows, and has one end connected to the medicine container B and the other end connected to a needle N insertable into a human body.

The heater cover 522 is a member extending along the first central axis C1 to correspond to the heater body 521, and is provided on a top surface of the heater body 521.

The heater cover 522 includes a semicircular tube accommodating groove 523 configured to surround and accommodate an upper part of the circular tube T.

The heater body 521 and the heater cover 522 are configured to cooperate with each other to 360°-surround a certain portion of the tube T.

Figure 5:
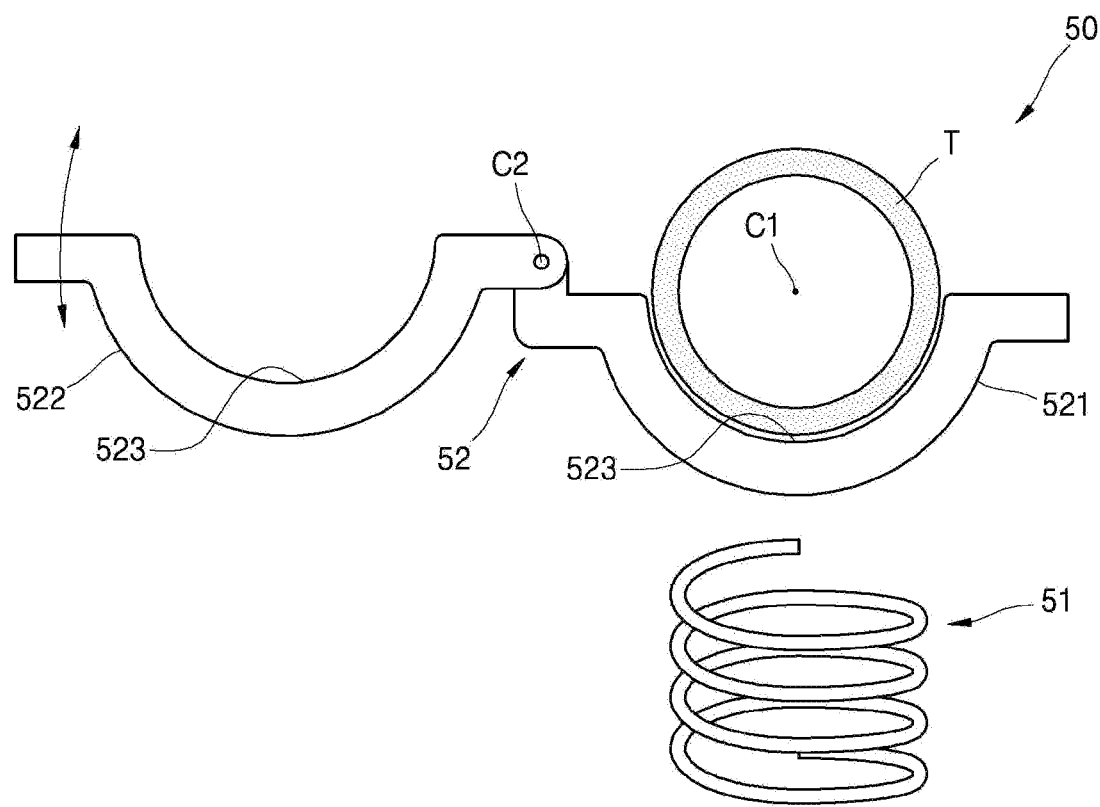
FIG. 5 is a top view illustrating that a heater cover of the heating unit illustrated in FIG. 4 is open.

The heater cover 522 is provided as a structure that is rotatable relatively to the heater body 521 about a second central axis C2 parallel with the first central axis C1 between a closed position for restraining the tube T and an open position for allowing the tube T to be taken out, as illustrated in FIG. 5.

The heater body 521 and the heater cover 522 may cooperate with each other to 360°-surround a certain portion of the tube T when the heater cover 522 is at the closed position, and the tube T may be inserted into or taken out of the tube accommodating groove 523 when the heater cover 522 is at the open position.

In the current embodiment, the pumps 11 and 21, the valves 15, 16, 17, 25, 26, and 27, the sensors 14 and 24, and the heating units 50 are automatically driven by a microcontroller unit (MCU) or the like, and are configured to accurately follow a preset medicine temperature, a dose per unit time, an infusion time, etc. by feedback control.

An example of a method of using the above-described medicine infusion apparatus 100 will now be described.

Initially, one medicine pressing unit 40 is mounted on the first outlet 13 and the other medicine pressing unit 40 is mounted on the second outlet 23 as illustrated in FIG. 1.

Subsequently, one medicine container B is inserted into the medicine container holder 42 of each of the two medicine pressing units 40. In this case, the tubes T are separately equipped with the heating units 50, and the needles N are inserted into a human body.

Figure 6:
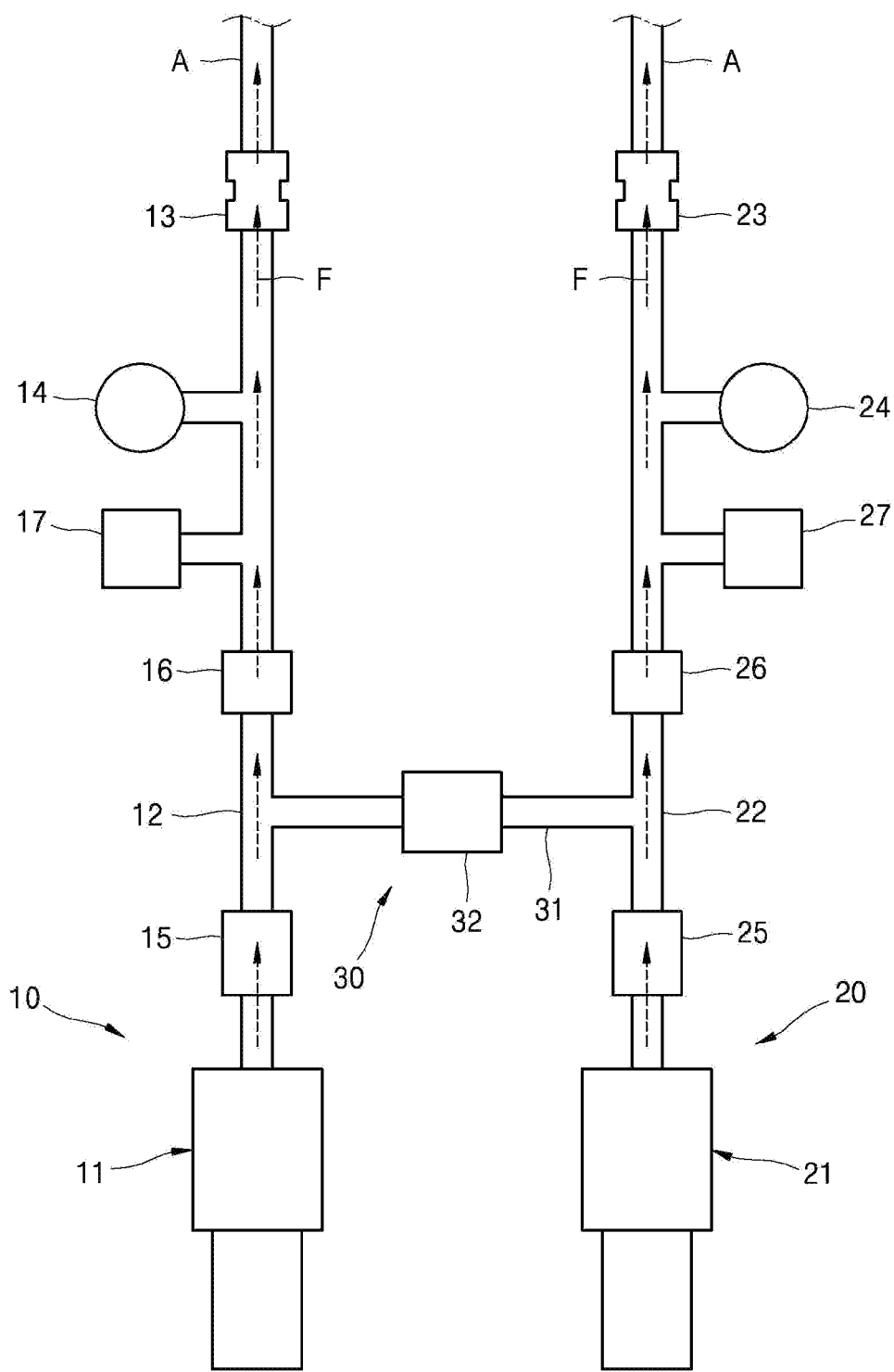
FIG. 6 is a front view illustrating that each of a first pumping unit and a second pumping unit is in charge of one of two medicine pressing units.

An air pressure desired by a user is set for each of the first and second pumping units 10 and 20, and the first and second pumps 11 and 21 are driven in such a manner that air flows F separately generated by the first and second pumps 11 and 21 proceed through the first and second pipes 12 and 22 as illustrated in FIG. 6 to inflate the inflatable parts 41 connected thereto. In this case, the first and second exhaust valves 17 and 27 and the connection pipe valve 32 are closed, and the first upstream valve 15, the first downstream valve 16, the second upstream valve 25, and the second downstream valve 26 are open.

That is, the first pumping unit 10 inflates one of the two inflatable parts 41, and the second pumping unit 20 inflates the other of the two inflatable parts 41.

When the two inflatable parts 41 inflate, the medicine containers B are pressed by the inflatable parts 41 and the medicine container holders 42 as illustrated in FIG. 3 and thus the medicine contained in the medicine containers B are infused into the human body through the tubes T and the needles N. In this case, the medicine flowing in the tubes T is heated to a preset temperature through the heating units 50.

In the current embodiment, when an air pressure sensed by the first sensor 14 is higher than a preset value, operation of the first pump 11 is temporarily stopped to block supply of air generated from the first pump 11 and, as necessary, the first exhaust valve 17 is open to reduce an internal air pressure of the inflatable part 41. Otherwise, when the air pressure sensed by the first sensor 14 is equal to or lower than the preset value, the first pump 11 may operate to increase the internal air pressure of the inflatable part 41.

While the first and second pumps 11 and 21 are operating, when the first pump 11 does not operate due to a failure or the like, the first sensor 14 senses the failure of the first pump 11 and the first upstream valve 15 is closed.

Figure 7:
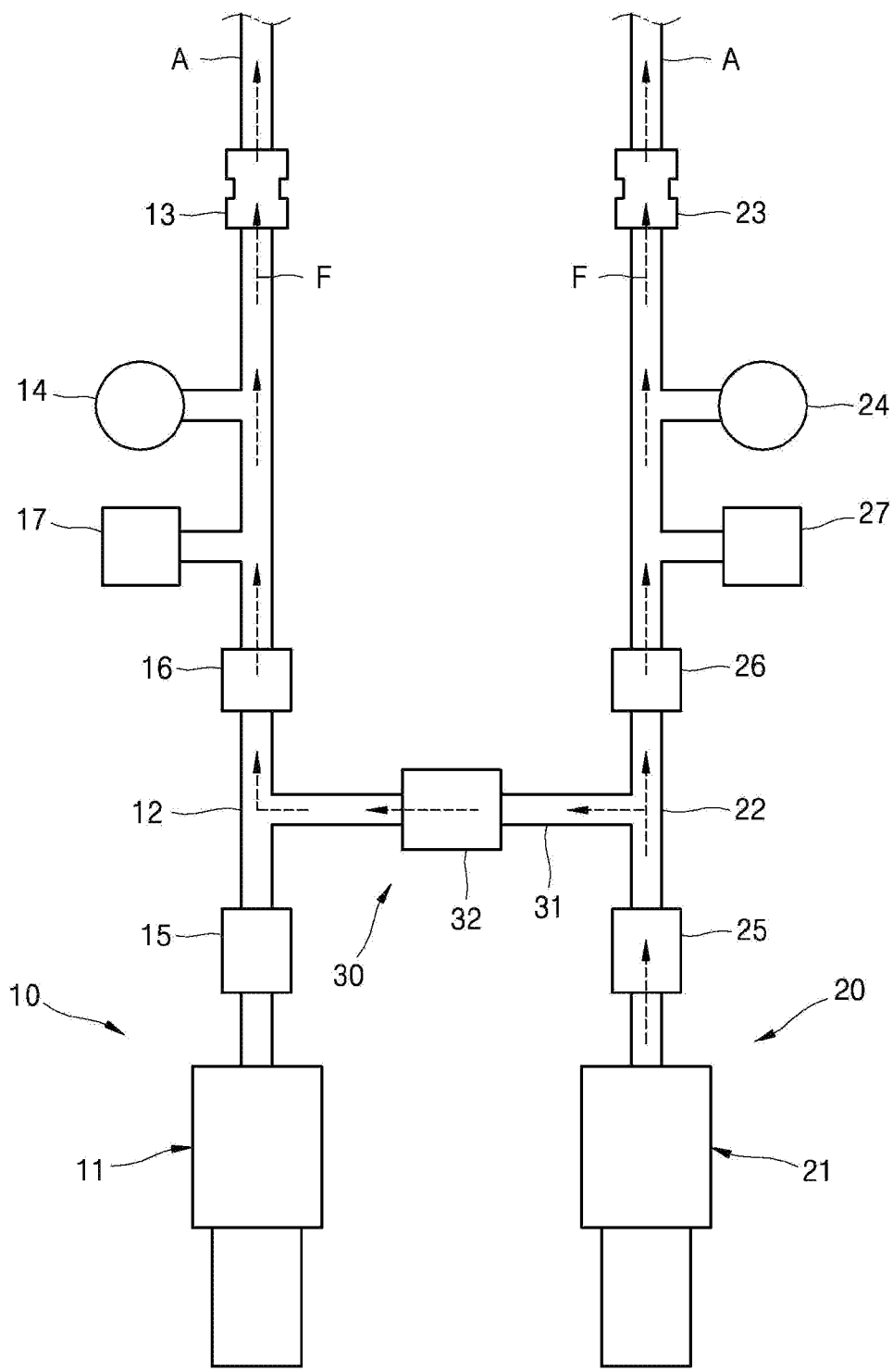
FIG. 7 is a front view illustrating that the second pump is in charge of the two medicine pressing units when the first pump does not operate.

Subsequently, the connection pipe valve 32 is open and thus the two medicine pressing units 40 are driven by the second pump 21 as illustrated in FIG. 7. This scheme may inflate one or more inflatable parts 41 connected to the first pipe 12 or/and the second pipe 22 by operating one of the first and second pumps 11 and 21 when the other of the first and second pumps 11 and 21 does not operate, and may be called a kind of fail safe driving scheme.

The above-described medicine infusion apparatus 100 is a medicine infusion apparatus capable of infusing a liquid medicine into a human body by using the medicine containers B each configured to discharge the liquid medicine contained therein, along a designated path when a pressure is applied from outside, and includes one or more medicine pressing units 40 including one or more inflatable parts 41 capable of being inflated by air to apply a pressure to the medicine container B, and the first pumping unit 10 capable of inflating one of the inflatable parts 41 by including the first pump 11 capable of generating air of a preset pressure, and the first pipe 12 connectable to the one of the inflatable parts 41. As such, a simple structure, a low failure rate, and a low total manufacturing cost may be achieved.

The medicine infusion apparatus 100 further includes the second pumping unit 20 capable of inflating one of the inflatable parts 41 by including the second pump 21 capable of generating air of a preset pressure, and the second pipe 22 connectable to the one of the inflatable parts 41. As such, two medicine pressing units 40 may simultaneously operate.

The medicine infusion apparatus 100 further includes the connection unit 30 including the connection pipe 31 for interconnecting the first and second pipes 12 and 22, and the connection pipe valve 32 capable of opening or closing the connection pipe 31, and one or more inflatable parts 41 connected to the first and second pipes 12 and 22 may be inflated by operating one of the first and second pumps 11 and 21 when the other of the first and second pumps 11 and 21 does not operate. As such, a fail safe driving scheme capable of operating the two medicine pressing units 40 when one of the first and second pumps 11 and 21 is broken may be implemented.

The medicine infusion apparatus 100 further includes the first upstream valve 15 provided at an upstream side of the first pipe 12, the first downstream valve 16 provided at a downstream side of the first pipe 12, the second upstream valve 25 provided at an upstream side of the second pipe 22, and the second downstream valve 26 provided at a downstream side of the second pipe 22, and the connection pipe 31 has one end connected to the first pipe 12 between the first upstream valve 15 and the first downstream valve 16, and the other end connected to the second pipe 22 between the second upstream valve 25 and the second downstream valve 26. As such, a fail safe driving scheme capable of operating one of the first and second pumps 11 and 21 in an emergency when the other of the first and second pumps 11 and 21 is broken may be implemented in a simple structure at a low cost.

The medicine infusion apparatus 100 further includes the heating units 50 for heating the medicine discharged from the medicine containers B, within a preset temperature range. As such, the medicine may be heated to an appropriate temperature and be instantaneously infused into the human body.

In the medicine infusion apparatus 100, the heating unit 50 operates in an IH manner by including the magnetic field generator 51 for generating a magnetic field and the heater 52 heated by a current induced by the magnetic field. As such, the medicine may be safely heated to an accurate temperature without thermally damaging other components.

In the medicine infusion apparatus 100, the heater 52 is configured to surround the tube T which is connected to the medicine container B and in which the medicine flows. As such, the medicine flowing in the tube T may be hygienically heated while the medicine is in the tube T.

In the medicine infusion apparatus 100, the medicine containers B may have a flexible bag shape. As such, the medicine containers B sold in the market may be conveniently and hygienically inserted into and used in the medicine container holders 42 of the medicine pressing units 40.

Figure 8:
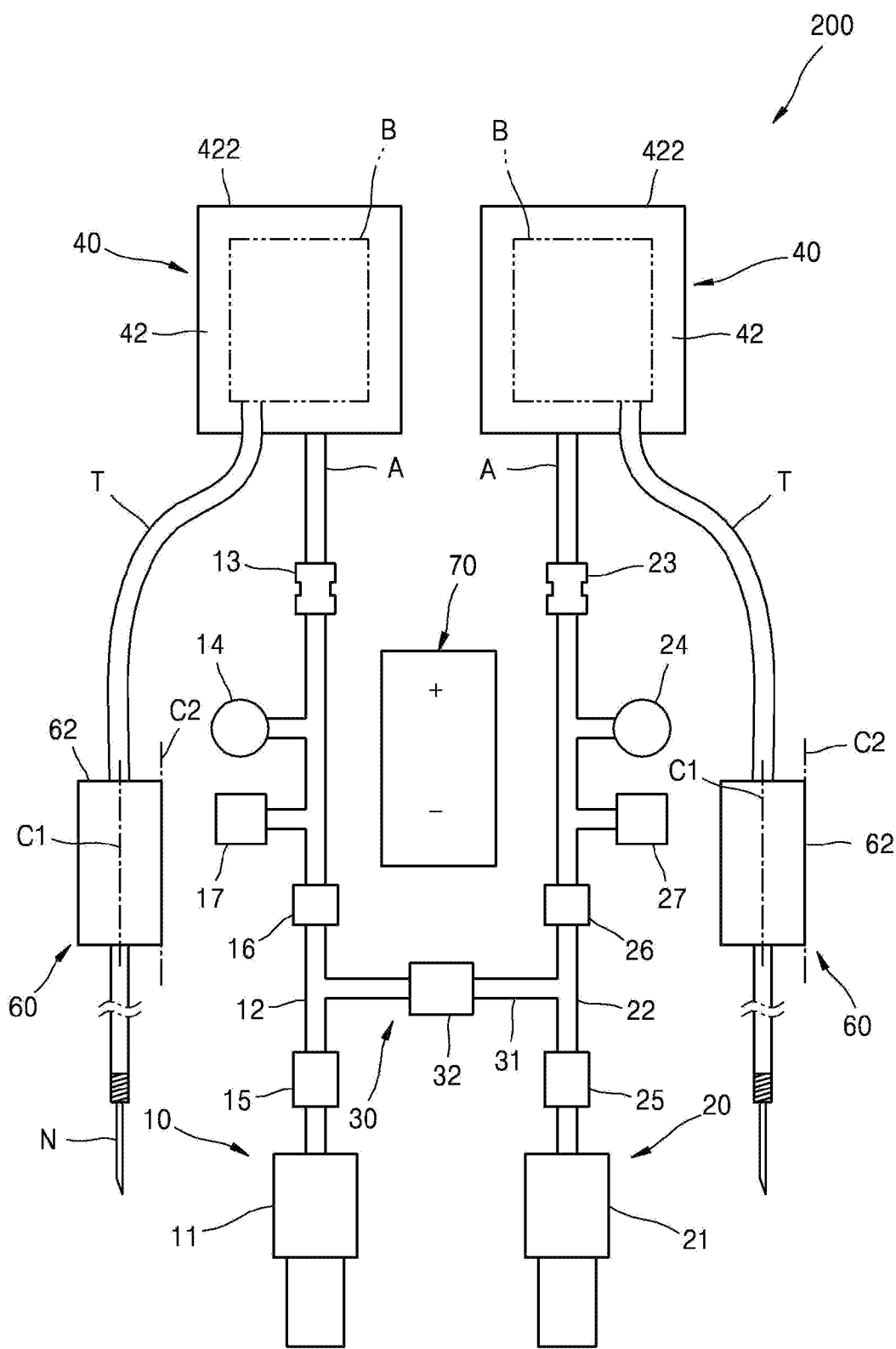
FIG. 8 is a front view of a medicine infusion apparatus according to a second embodiment of the present invention.

FIG. 8 is a front view of a medicine infusion apparatus 200 according to a second embodiment of the present invention. The elements and effects of the medicine infusion apparatus 200 are mostly the same as those of the above-described medicine infusion apparatus 100, and thus the following description is focused on differences therebetween.

The medicine infusion apparatus 200 includes new heating units 60 instead of the heating units 50, and further includes a battery 70.

Each of the heating units 60 includes a heating unit body 61, a heating unit cover 62, and a thermoelectric module 63.

The heating unit body 61 is a rectangular container including a heating space 67 therein, and includes semicircular through holes 64 in top and bottom surfaces thereof.

In the current embodiment, the heating unit body 61 is made of a metal material having a high thermal conductivity.

A diameter of the through holes 64 may be the same as a diameter of the tube T or be slightly less than the diameter of the tube T within a tolerance range.

The heating space 67 is a sealed space capable of accommodating the tube T to be isolated from outside.

The heating unit cover 62 is a rectangular cover having a shape corresponding to the heating unit body 61, and is a member for closing the heating space 67.

In the current embodiment, the heating unit cover 62 is made of a synthetic resin material having a low thermal conductivity.

The heating unit cover 62 includes semicircular through holes 64 in top and bottom surfaces thereof.

In the current embodiment, the heating unit cover 62 is coupled to the heating unit body 61 by hinges 65 to be rotatable between a closed position for closing the heating space 67 and an open position for opening the heating space 67.

When the heating unit cover 62 is at the closed position, the heating unit body 61 and the heating unit cover 62 cooperate with each other to form the heating space 67.

The through holes 64 of the heating unit cover 62 are provided at locations corresponding to the through holes 64 of the heating unit body 61.

Therefore, when the heating unit cover 62 is at the closed position, the through holes 64 of the heating unit cover 62 cooperate with the through holes 64 of the heating unit body 61 to form a pair of circular holes through which the tube T may penetrate.

The thermoelectric module 63 is a heat source capable of heating a medicine in the tube T within a preset temperature range, and is a thermoelectric module using the Peltier effect (or the thermoelectric effect).

The thermoelectric module 63 is a member having a thin flat panel shape, and is attached to a rear surface of the heating unit body 61.

A detailed configuration of the thermoelectric module 63 is well known to one of ordinary skill in the art, and thus a detailed description thereof is not provided herein.

The Peltier effect (or the thermoelectric effect) is an effect discovered in 1834 and theoretically established in the early 1900s, and is also called thermoelectric refrigeration technology.

The Peltier effect was introduced by the French physicist Jean Charles Athanase Peltier, and refers to an effect that heat of a low-temperature side to be cryogenically cooled is transferred to a high-temperature side opposite to the low-temperature side by forcibly cooling the high-temperature side by using a phenomenon in which a temperature difference between both ends of multiple conductive layers is continued when a current is supplied.

Herein, when one side is cooled, the other side is heated due to the Seebeck effect. A heated surface needs to be cooled well to increase efficiency and, when overheated, efficiency may be reduced and, more seriously, a thermoelectric device may be broken or a low-temperature side and a high-temperature side may be switched due to the conversion of heat.

One of the greatest advantages of the thermoelectric module 63 is that a cooling effect may be achieved without using a separate refrigerant or a driver and thus a simple structure and a low failure rate may be achieved.

In addition, the thermoelectric module 63 may be produced in a thin flat panel shape and thus a compact size, portability, and precise temperature control may be enabled.

However, a disadvantage of the thermoelectric module 63 is that the thermoelectric module 63 has a low coefficient of performance (COP) indicating energy efficiency compared to a general cooler and thus is not suitable for high-capacity cooling or heating.

The tube T may be densely arranged at a preset density or above in the heating space 67.

Figure 9:
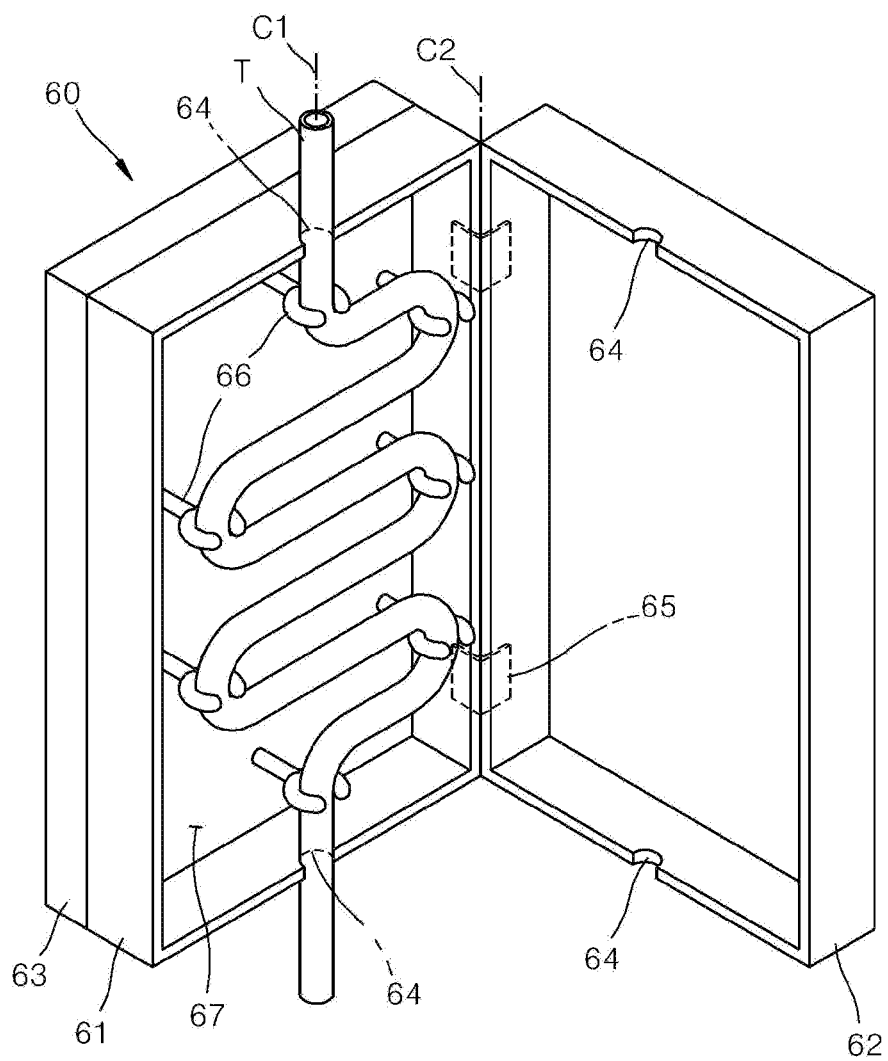
FIG. 9 is a perspective view of a heating unit illustrated in FIG. 8.
Figure 10:
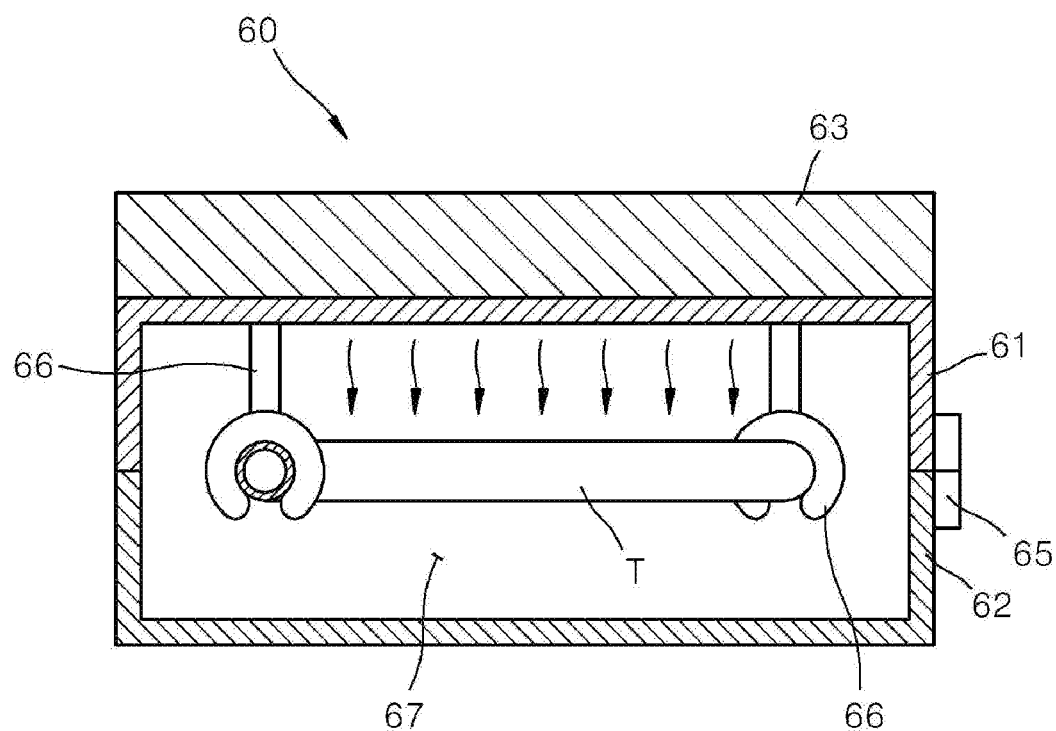
FIG. 10 is a horizontal cross-sectional view of the heating unit illustrated in FIG. 8.

In the current embodiment, the tube T may be provided in a zigzag shape in the heating space 67 as illustrated in FIG. 9.

Because a direct contact between the tube T, and the heating unit body 61 and the thermoelectric module 63 is not preferable, the tube T is provided not to directly contact the heating unit body 61 and the heating unit cover 62 in the current embodiment.

In the current embodiment, a plurality of tube fixers 66 capable of detachably fixing the tube T may be mounted in the heating unit body 61.

Figure 11:
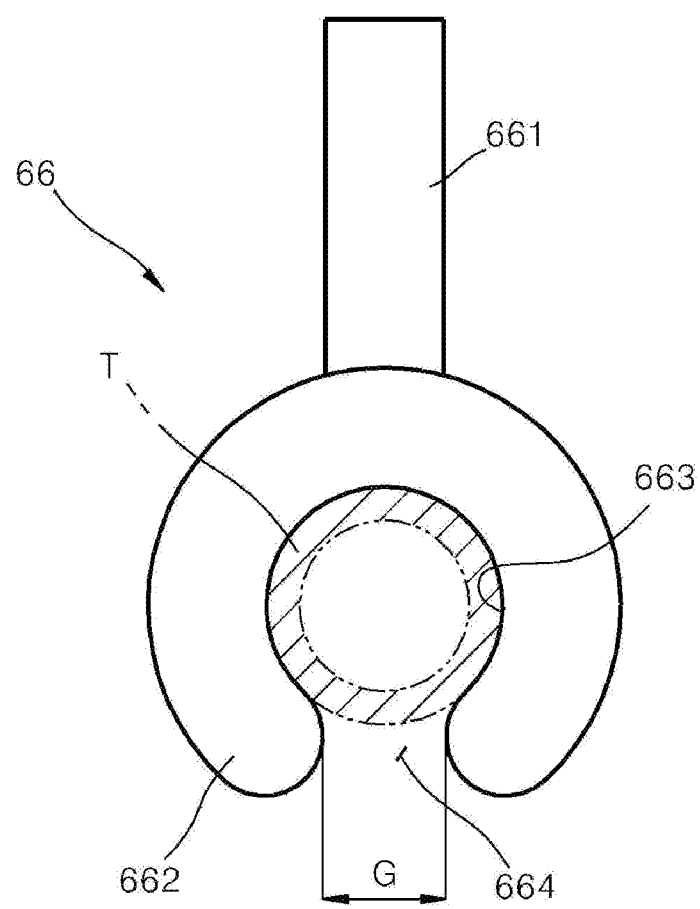
FIG. 11 is a top view of a tube fixer illustrated in FIG. 9.

Each of the tube fixers 66 includes a fixing part 661, a gripping part 662, and an insertion part 664 as illustrated in FIG. 11, and is made of a synthetic resin material having a low thermal conductivity.

The fixing part 661 has one end coupled to the heating unit body 61 and the other end coupled to the gripping part 662, and is a part for spacing the gripping part 662 apart from the heating unit body 61 by a preset distance.

The gripping part 662 is a part for gripping and fixing the tube T, is elastically deformable, and includes a hollow hole 663 therein.

A diameter of the hollow hole 663 may be the same as a diameter of the tube T or be slightly less than the diameter of the tube T within a tolerance range.

The insertion part 664 is a passage through which the tube T is inserted into the hollow hole 663, and is provided at one end of the hollow hole 663.

A width G of the insertion part 664 may be less than the diameter of the tube T.

In the current embodiment, the tube fixer 66 may operate in a snap-fit manner based on the above configuration. That is, the width G of the insertion part 664 increases when the tube T enters through the insertion part 664, and returns to normal when the tube T is fixed in the hollow hole 663.

In the current embodiment, the tube T contacts only the tube fixers 66 and does not directly contact the heating unit body 61, the heating unit cover 62, and the thermoelectric module 63.

Therefore, the heating unit 60 has a configuration in which the thermoelectric module 63 may heat air contained in the heating space 67 and the heated air may indirectly heat the tube T.

The battery 70 is a replaceable battery or a rechargeable battery and is a battery for supplying electricity to the medicine infusion apparatus 200.

The above-described medicine infusion apparatus 200 includes the heating units 60 each including the thermoelectric module 63 capable of heating the medicine within a preset temperature range. As such, the medicine infusion apparatus 200 may be produced as a compact portable apparatus by using the low-capacity battery 70 and be used for emergencies at accident sites where electricity may not be easily supplied.

In the medicine infusion apparatus 200, the heating unit 60 includes the heating space 67 capable of accommodating the tube T, in which the medicine flows, to be isolated from outside, and the thermoelectric module 63 may heat air contained in the heating space 67 and the heated air may indirectly heat the tube T. As such, the medicine in the tube T may be uniformly heated to a preset temperature, and spoiling of the medicine and damage of the tube T due to overheating may be prevented.

In the medicine infusion apparatus 200, the tube T is densely arranged at a preset density or above in the heating space 67. As such, a heating rate and energy efficiency may be increased based on the same electricity.

In the medicine infusion apparatus 200, the heating unit 60 includes the tube fixers 66 capable of detachably fixing the tube T in which the medicine flows. As such, the tube T may be firmly fixed in the heating unit 60.

In the medicine infusion apparatus 200, the tube fixer 66 includes the gripping part 662 including the hollow hole 663 capable of accommodating the tube T, and being elastically deformable, and the insertion part 664 provided at one end of the hollow hole 663 to serve as a passage through which the tube T is inserted into the hollow hole 663. As such, the tube fixer 66 may operate in a snap-fit manner.

In the medicine infusion apparatus 200, the heating unit 60 includes the heating unit body 61 including the heating space 67 capable of accommodating the tube T, in which the medicine flows, to be isolated from outside, and the heating unit cover 62 capable of changing positions between a closed position for closing the heating space 67 and an open position for opening the heating space 67, and the through holes 64 capable of detachably accommodating the tube T are provided in at least one of the heating unit body 61 and the heating unit cover 62. As such, the tube T included in a general fluid bag set may be conveniently equipped with the heating unit 60.

In the medicine infusion apparatus 200, the heating unit cover 62 of the heating unit 60 is coupled to the heating unit body 61 by the hinges 65 to be rotatable between the closed position and the open position. As such, the heating space 67 may be easily open or closed.

The medicine infusion apparatus 200 receives electricity supplied by the replaceable or rechargeable battery 70. As such, the medicine infusion apparatus 200 may be produced as a compact portable apparatus and be used for emergencies at accident sites where electricity may not be easily supplied.

Although a pair of the medicine pressing units 40 are separately connected to the first and second pumping units 10 and 20 in the above-described embodiments, the second pumping unit 20 may not be included and only one medicine pressing unit 40 may be connected to one first pumping unit 10.

Although an internal air pressure of the inflatable part 41 is controlled by temporarily stopping operation of the first or second pump 11 or 21 or by temporarily opening the first or second exhaust valve 17 or 27 in the above-described embodiments, the internal air pressure of the inflatable part 41 may also be controlled by temporarily closing or opening the first downstream valve 16 or the first upstream valve 15 or temporarily opening the first or second exhaust valve 17 or 27.

While the present invention has been particularly shown and described with reference to embodiments thereof, it will be understood by one of ordinary skill in the art that various changes in form and details may be made therein without departing from the spirit and scope of the present invention as defined by the following claims.

The invention claimed is:

1. A medicine infusion apparatus capable of infusing a liquid medicine into a human body by using a medicine container configured to discharge the liquid medicine contained therein, along a designated path when a pressure is applied from outside, the medicine infusion apparatus comprising:
   one or more medicine pressing units comprising one or more inflatable parts capable of being inflated by air to apply a pressure to the medicine container;
   a first pumping unit capable of inflating one of the inflatable parts by comprising a first pump capable of generating air of a preset pressure, and a first pipe connectable to the one of the inflatable parts;
   a second pumping unit capable of inflating one of the inflatable parts comprising a second pump capable of generating air of a preset pressure, and a second pipe connectable to the one of the inflatable parts;
   a connection unit comprising a connection pipe for interconnecting the first and second pipes, and a connection pipe valve capable of opening or closing the connection pipe;
   a first sensor measuring an internal air pressure of the first pipe;
   a second sensor measuring an internal air pressure of the second pipe; and
   a heating unit comprising a thermoelectric module capable of heating the medicine within a preset temperature range,
   wherein one or more inflatable parts connected to the first and second pipes are inflated by operating one of the first and second pumps when another of the first and second pumps does not operate, and
   wherein a failure of the first pump or a failure of the second pump is sensed by the first sensor or the second sensor.

2. The medicine infusion apparatus of claim 1, further comprising:
   a first upstream valve provided at an upstream side of the first pipe;
   a first downstream valve provided at a downstream side of the first pipe;
   a second upstream valve provided at an upstream side of the second pipe; and
   a second downstream valve provided at a downstream side of the second pipe,
   wherein the connection pipe has one end connected to the first pipe between the first upstream valve and the first downstream valve, and another end connected to the second pipe between the second upstream valve and the second downstream valve.

3. The medicine infusion apparatus of claim 1, wherein the heating unit comprises a heating space capable of accommodating a tube, in which the medicine flows, to be isolated from outside, and
   wherein the thermoelectric module heats air contained in the heating space and the heated air indirectly heats the tube.

4. The medicine infusion apparatus of claim 3, wherein the tube is densely arranged at a preset density or above in the heating space.

5. The medicine infusion apparatus of claim 1, wherein the heating unit comprises a tube fixer capable of detachably fixing a tube in which the medicine flows.

6. The medicine infusion apparatus of claim 5, wherein the tube fixer comprises:
   a gripping part comprising a hollow hole capable of accommodating the tube, and being elastically deformable; and
   an insertion part provided at one end of the hollow hole to serve as a passage through which the tube is inserted into the hollow hole.

7. The medicine infusion apparatus of claim 1, wherein the heating unit comprises:
   a heating unit body comprising a heating space capable of accommodating a tube, in which the medicine flows, to be isolated from outside; and
   a heating unit cover capable of changing positions between a closed position for closing the heating space and an open position for opening the heating space, and
   wherein through holes capable of detachably accommodating the tube are provided in at least one of the heating unit body and the heating unit cover.

8. The medicine infusion apparatus of claim 7, wherein the heating unit cover of the heating unit is coupled to the heating unit body by hinges to be rotatable between the closed position and the open position.

9. The medicine infusion apparatus of claim 1, wherein the medicine infusion apparatus receives electricity supplied by a replaceable or rechargeable battery.

* * * * *